(12) United States Patent
Brunner

(10) Patent No.: US 9,255,887 B2
(45) Date of Patent: Feb. 9, 2016

(54) 2D PROGRAMMABLE APERTURE MECHANISM

(71) Applicant: KLA-Tencor Corporation, Milpitas, CA (US)

(72) Inventor: Rudolf Brunner, Menlo Park, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/304,373

(22) Filed: Jun. 13, 2014

(65) Prior Publication Data

US 2014/0375987 A1    Dec. 25, 2014

Related U.S. Application Data

(60) Provisional application No. 61/837,034, filed on Jun. 19, 2013.

(51) Int. Cl.
| | | |
|---|---|---|
| *G01N 21/00* | (2006.01) | |
| *G01N 21/88* | (2006.01) | |
| *G01N 21/95* | (2006.01) | |
| *G02B 26/02* | (2006.01) | |

(52) U.S. Cl.
CPC ........ *G01N 21/8806* (2013.01); *G01N 21/9501* (2013.01); *G02B 26/02* (2013.01)

(58) Field of Classification Search
None
See application file for complete search history.

(56) References Cited

U.S. PATENT DOCUMENTS

| | | |
|---|---|---|
| 7,345,754 B1 | 3/2008 | Zhao et al. |
| 7,630,069 B2 | 12/2009 | Naftali et al. |
| 8,115,926 B2 | 2/2012 | Straaijer |
| 8,289,509 B2 | 10/2012 | Wenz |
| 2004/0218291 A1 | 11/2004 | Fiete |
| 2009/0232491 A1 | 9/2009 | Masuda et al. |
| 2011/0284747 A1 | 11/2011 | Powell et al. |
| 2012/0293794 A1 | 11/2012 | Gutman |
| 2013/0148115 A1 | 6/2013 | Berlatzky et al. |

FOREIGN PATENT DOCUMENTS

| | | |
|---|---|---|
| EP | 0971218 A2 | 12/2000 |
| WO | 2011003208 A1 | 1/2011 |
| WO | 2013005582 A1 | 10/2013 |

OTHER PUBLICATIONS

International Search Report and Written Opinion mailed on Oct. 15, 2014, for PCT Application No. PCT/US2014/043277 filed on Jun. 19, 2014, by KLA-Tencor Corporation, 9 pages.

*Primary Examiner* — Tri T Ton
(74) *Attorney, Agent, or Firm* — Spano Law Group; Joseph S. Spano

(57) ABSTRACT

Methods and systems for reconfiguring an aperture of an optical inspection system are presented. A programmable aperture system includes a two dimensional array of mechanical pixels that selectively block light passing through the aperture. An array of linear guiding elements is aligned parallel to one another, and each row of mechanical pixels is supported by a corresponding linear guiding element. Each mechanical pixel is configured to slide along the corresponding linear guiding element when pushed by an actuator subsystem. The actuator subsystem repositions one or more of the mechanical pixel elements to change the shape of the aperture. The actuator subsystem is configured to selectively engage one or more mechanical pixel elements and translate the one or more mechanical pixel elements along corresponding linear guiding elements to a new position.

18 Claims, 6 Drawing Sheets

2D PROGRAMMABLE APERTURE MECHANISM

CROSS REFERENCE TO RELATED APPLICATION

The present application for patent claims priority under 35 U.S.C. §119 from U.S. provisional patent application Ser. No. 61/837,034, entitled "2D Programmable Aperture Mechanism," filed Jun. 19, 2013, the subject matter of which is incorporated herein by reference in its entirety.

TECHNICAL FIELD

The described embodiments relate to optical inspection systems and methods, and more particularly to methods and systems for improved aperture mechanisms for shaping light within an optical inspection system.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Optical inspection processes are used at various steps during a semiconductor manufacturing process to detect defects on wafers to promote higher yield. Optical inspection techniques offer the potential for high throughput without the risk of sample destruction.

Optical apertures with differing shapes and sizes are employed to manipulate illumination and imaging properties in optical systems. In particular, optical aperture shape and size may be tuned to increase the measurement signal to noise ratio for a specific wafer pattern, defect of interest, etc.

In some examples, an iris mechanism with adjustable blades, e.g., a traditional camera shutter mechanism, is employed as an adjustable aperture mechanism. The aperture size is varied by moving the blades between an open position and a closed position. Although the size of the aperture is fully adjustable, the shape of the aperture is determined by the size, and is limited to an approximately circular shape that scales in size as the blades move between the open and closed positions.

In some other examples, a rotating wheel including multiple apertures is selectively positioned such that a desired aperture shape is positioned in an optical beam path. However, the number of aperture shapes and sizes is limited by the number of predetermined apertures available on a particular wheel.

In some other examples a linear slider mechanism includes multiple apertures selectively positioned such that a desired aperture shape is positioned in an optical beam path. Again, the number of aperture shapes and sizes is limited by the number of predetermined apertures available on a particular linear slider. In some examples, a tape drive mechanism positions a desired aperture shape printed on a thin tape. The tape is positioned by rotating reels on both ends of the tape. Similarly, the number of shapes that can be presented by the tape drive mechanism is limited by the number of predetermined apertures available on the particular tape.

Liquid crystal arrays may be employed as programmable aperture mechanisms. However, liquid crystal arrays suffer from a number of practical limitations. Firstly, liquid crystal array pixels are not fully transmissive when programmed in a transmissive mode. This leads to excessive light loss. This is particularly costly in the context of a modern inspection system. Secondly, liquid crystal array pixels are not fully occluding in a blocking mode. This leads to excessive light leakage that is detrimental in a modern optical inspection system. Moreover, liquid crystal arrays may also induce stray light, scattered light, and optical aberrations that further degrade optical inspection performance. Furthermore, liquid crystal arrays may also suffer from limited lifetime when exposed to short wavelength light, particularly at high power densities.

Tilt mirror arrays may also be employed as programmable aperture mechanisms. However, tilt mirror arrays also suffer from light loss and optical artifacts such as stray light, scattered light, and optical aberrations that limit optical inspection system performance.

In some examples, aperture patterns have been exposed and developed on photofilm. However, photofilm systems, are not completely transmissive and completely occlusive, leading to undesirable light loss and light leakage. Moreover, exposure and development of photofilms is costly and time consuming, and the resulting films have a low damage threshold. Photofilm systems may also cause contamination of other elements of UV, DUV, and VUV light systems commonly employed in modern inspection systems.

In some other examples, aperture patterns have been applied onto transmissive substrates by inkjet printing. However, inkjet printing systems are not completely transmissive and completely occlusive, leading to undesirable light loss and light leakage. Moreover, inkjet systems require either a consumable substrate or a substrate that must be recleaned, leading to cost and throughput issues. Printed substrates may also cause contamination of other elements of UV, DUV, and VUV light systems commonly employed in modern inspection systems.

In some other examples, Fourier filters (e.g., a plurality of metal bars with adjustable spacing) have also been employed as flexible optical apertures. U.S. Pat. No. 5,970,168, which is incorporated herein by reference in its entirety, describes an example of a Fourier filter. However, Fourier filters allow for very few shapes and are typically employed for the limited purpose of blocking diffraction patterns.

In some other examples, a microshutter array, such as the array of microelectromechanical shutters employed as part of the James-Webb space telescope, may also be employed as a programmable aperture mechanism. However, microshutter arrays may suffer from excessive light loss in a transmissive mode due to the array structure. In addition, the arrays structure may induce stray light effects. Moreover, microshutter arrays are complex devices that give rise to cost and reliability issues.

As described hereinbefore, previous flexible optical aperture systems have several disadvantages such as optical transmission losses, incomplete optical blocking, stray light, optical aberrations, limited shape flexibility or spatial resolution, low damage threshold, and incompatibility with short wavelength light. Thus, methods and systems for improved programmable aperture mechanisms operable in modern optical inspection tools are desired.

SUMMARY

Methods and systems for reconfiguring an aperture of an optical inspection system are presented. In one aspect, a programmable aperture system includes a two dimensional array of mechanical pixels that selectively blocks light passing through the aperture. An array of linear guiding elements is aligned parallel to one another, and each row of mechanical pixels is supported by a corresponding linear guiding element. Each mechanical pixel is configured to slide along the corresponding linear guiding element when pushed by an actuator subsystem. The actuator subsystem repositions one or more of the mechanical pixel elements to change the shape of the aperture. The actuator subsystem is configured to selectively engage one or more mechanical pixel elements and translate the one or more mechanical pixel elements along corresponding linear guiding elements to a new position.

The shape of the aperture formed by the array of mechanical pixels is reconfigured to form any number of different shapes by arranging the array of mechanical pixels. Multiple openings along each linear guiding element may be created by engaging different mechanical pixels at different locations and selectively sliding the engaged pixels along the corresponding linear guiding element.

Each mechanical pixel includes a surface that may be exposed to incoming light. In some embodiments, the surface is highly absorptive, or treated with a highly absorptive coating, to absorb incoming light. In this manner, light that is blocked by the mechanical pixel is absorbed and stray reflections that may interfere with the performance of the optical inspection system are minimized. To dissipate heat accumulated by the mechanical pixel element, a cooling system such as forced air cooling, liquid immersion, or radiative cooling may be employed. In some other embodiments, the surface is highly reflective to avoid excessive heat accumulation in each mechanical pixel. In some of these embodiments, the surface is tilted such that the normal to the surface is not aligned with the beam of incoming light. In this manner, light reflected from the surface is directed away from the beam of light passing through the programmable aperture.

In some embodiments, each mechanical pixel includes one or more protrusion features configured to overlap with complementary features located adjacent mechanical pixels. In combination, these complementary features create a light trap that prevents the transmission of light through any nominal gap between pixels.

In some embodiments, the linear guiding elements are wire elements stretched across the aperture area. The cross-section of the wire elements may be rectangular in shape to constrain the position of each mechanical pixel in five degrees of freedom while presenting a small cross-sectional area exposed to the incoming beam of light. In some other embodiments, a wire element with a T-shaped cross-section may be employed to prevent incoming light from grazing the side of the wire element.

In some other embodiments, the linear guiding elements are extensible structures (e.g., telescoping beams) selectively positioned across the aperture area. The position of each extensible structure across the aperture area can be reconfigured along with the locations of the mechanical pixels attached to each extensible structure. In this manner, the aperture can be reconfigured to realize any number of different shapes.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for reconfiguring an aperture of an optical inspection system are presented. Such systems are employed to measure structural and material characteristics (e.g., material composition, dimensional characteristics of structures and films, etc.) associated with different semiconductor fabrication processes.

An aperture mechanism programmable in two dimensions is introduced to increase the range of measurement applications accommodated by the measurement system with increased sensitivity, while maintaining adequate throughput necessary for modern semiconductor manufacture.

Figure 1:
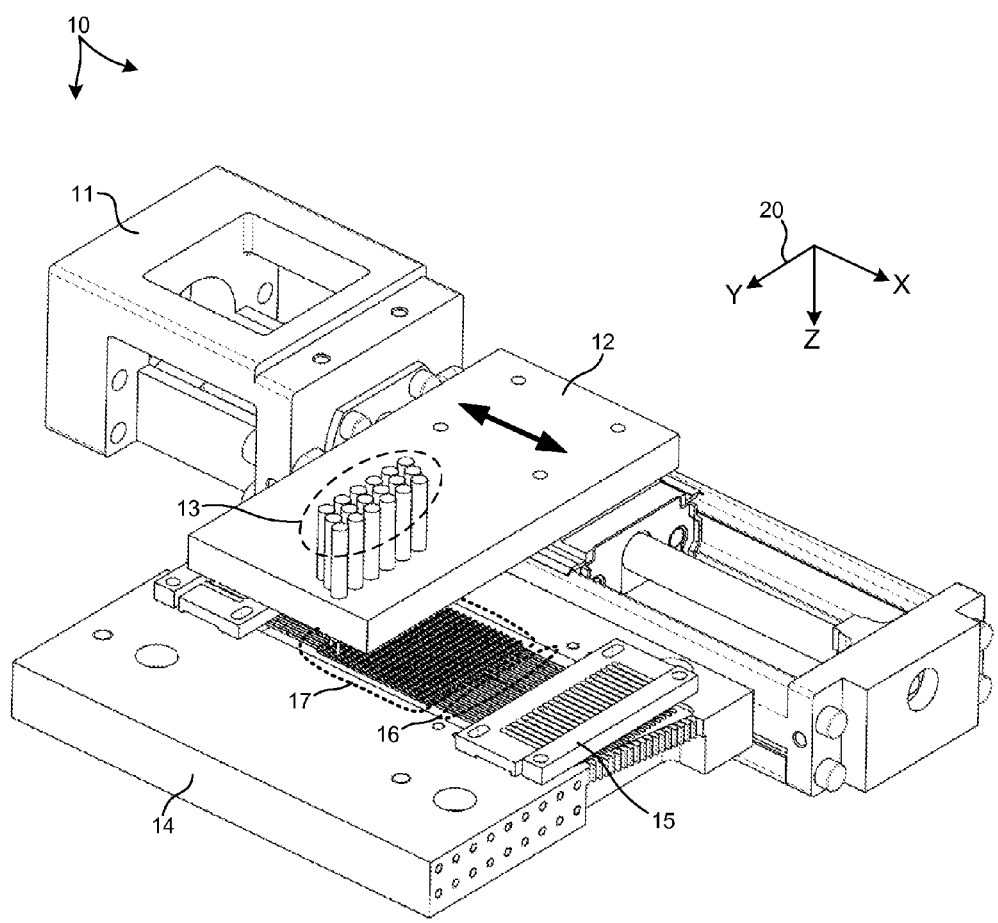
FIG. 1 is a schematic view illustrative of a programmable aperture system that includes a two dimensional array of mechanical pixels that selectively blocks light passing through an aperture.

FIG. 1 illustrates a programmable aperture system 10 in one embodiment. The programmable aperture system 10 includes a two dimensional array of mechanical pixels 17 that selectively block light passing through the aperture formed by the intersection of the array of mechanical pixels 17 and an optical beam (not shown). An array of linear guiding elements 16 are fixed to a frame 14 and are aligned parallel to one another. In the embodiment depicted in FIG. 1, each of the linear guiding elements 16 is aligned with the x-direction of coordinate frame 20. Each row of mechanical pixels 17 is supported by a linear guiding element of the array 16. The linear guiding elements are tensioned by a frame 15 including an array of leaf springs in contact with a corresponding linear guiding element.

In the embodiment depicted in FIG. 1, each mechanical pixel is mechanically constrained by a corresponding linear guiding element. In some embodiments, each mechanical pixel is constrained in five degrees of freedom by a corresponding linear guiding element, and is constrained in the sixth degree of freedom by a frictional contact between each mechanical pixel and the corresponding linear guiding element. In this manner, each mechanical pixel is free to slide along the linear guiding element when pushed by a force that exceeds the frictional contact force. The mechanical pixels are designed with an appropriate amount of frictional contact between each mechanical pixel and a corresponding linear guiding element. In this manner, each mechanical pixel remains fixed in position relative to the corresponding linear guiding element when subjected to expected gravitational and disturbance forces.

In the embodiment depicted in FIG. 1, an 18×18 array of mechanical pixels is available to form a reconfigurable aperture spanning a beam diameter of 21.96 millimeters. The linear guiding elements are separated by 1.22 millimeters. When the pixels are all located out of the path of the optical beam, the transmission efficiency is greater than ninety percent.

In one aspect, the shape of the aperture formed by the array of mechanical pixels is reconfigured to form any number of different shapes by arranging the array of mechanical pixels. More specifically, the aperture shape is changed by sliding one or more of the mechanical pixels to different locations on each corresponding linear guiding element. An actuator subsystem is configured to selectively engage one or more features of one or more mechanical pixel elements and translate the one or more mechanical pixel elements along corresponding linear guiding elements to a new position. In the embodiment depicted in FIG. 1, a linear actuator 11 is configured to translate a frame 12 in a direction parallel to the direction of each of the linear guiding elements 16 (i.e., the x-direction). An array of engagement actuators 13 is configured to selectively engage mechanical pixels from each row.

In the depicted embodiment, each of the array of engagement actuators 13 is a solenoid actuator. However, in general many types of actuators may be contemplated to selectively engage the mechanical pixel elements. For example, electromagnetic actuators such as a linear motor, Lorentz coil, or an electro magnet acting directly on the mechanical pixel, pneumatic actuators such as a pneumatic cylinder or gas jet, piezoelectric actuators, shape memory alloy actuators, etc. may be contemplated. In some embodiments linear actuator 11 is configured to translate in two degrees of freedom (e.g., x and y directions). In this manner, one or more engagement actuators 13 can separately engage mechanical pixels on different linear guiding elements. In general, any number of actuator system architectures may be employed to selectively engage any of the mechanical pixels of the array 17.

Figure 2:
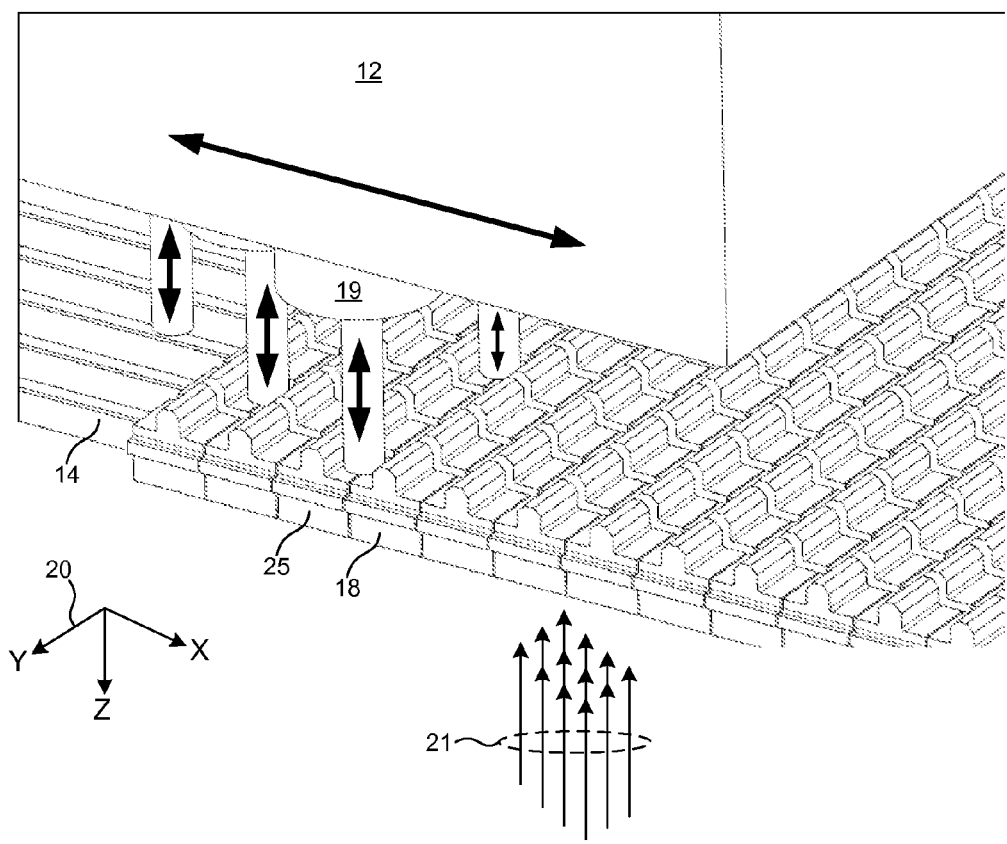
FIG. 2 illustrates a more detailed view of the programmable aperture system depicted in FIG. 1, including a linear actuator engaging a mechanical pixel.

FIG. 2 illustrates a more detailed view of system 10 depicted in FIG. 1. FIG. 2 depicts a linear actuator 19 of the array of linear actuators 13 that has moved in the z-direction and has engaged a mechanical pixel 18. Following the movement to the engaged position, a movement of frame 12 in the x-direction slides mechanical pixel 18, and any pixels in its path, along the linear guiding element 14. This generates an opening between mechanical pixel 18 and mechanical pixel 25. This enables a portion of light beam 21 to pass through the gap created between pixels 18 and 25. Similarly, each linear actuator of the array 13 may engage different mechanical pixels in different locations along each linear guiding element. Subsequent movements of frame 12 along the x-direction create the same or different openings in the array of mechanical pixels along each linear guiding element. Multiple openings along each linear guiding element may be created by engaging different mechanical pixels at different locations and selectively sliding the engaged pixels along the corresponding linear guiding element.

Figure 3:
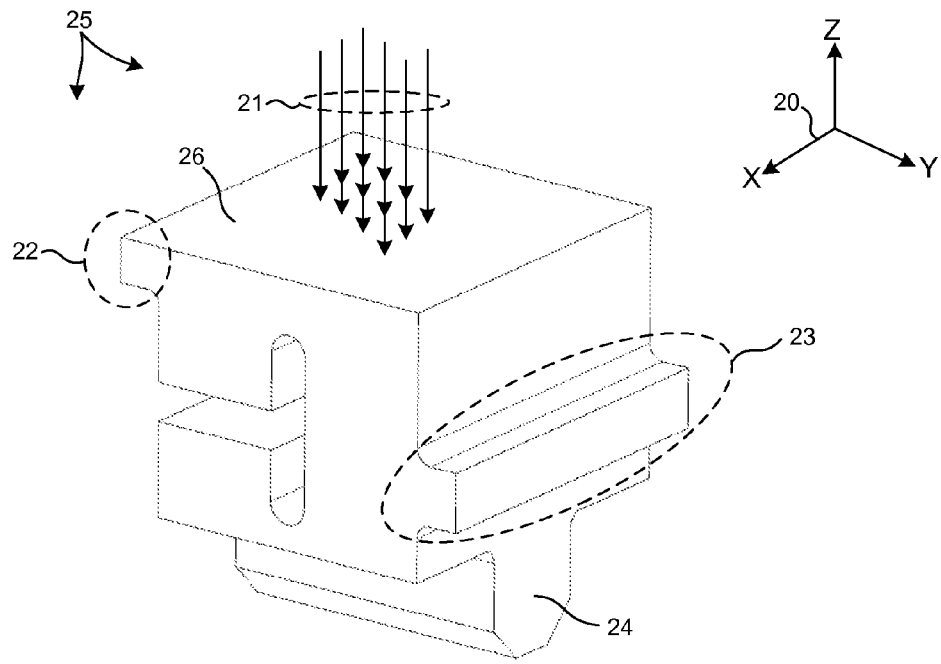
FIG. 3 illustrates a more detailed view of a mechanical pixel associated with the embodiment described with reference to FIG. 1.

FIG. 3 depicts a mechanical pixel 25 associated with the embodiment described with reference to FIG. 1. As depicted in FIG. 3, each mechanical pixel includes a surface 26 exposed to incoming light 21 and an engaging feature 24 on the backside of the mechanical pixel. Engaging feature 24 is shaped such that the linear actuators of array 13 can engage and slide the mechanical pixel along the corresponding linear guiding element. In one embodiment, each mechanical pixel is constructed from Aluminum using a wire electro-discharge machining process.

In some embodiments, surface 26 may be highly absorptive, or treated with a highly absorptive coating, to absorb incoming light. In this manner, light that is blocked by the mechanical pixel is absorbed and stray reflections that may interfere with the performance of the optical inspection system are minimized. When surface 26 exposed to the beam of incoming light 21 is highly absorptive, mechanical pixel 25 will accumulate significant heat due to the high intensity nature of light 21 employed in typical semiconductor inspection systems. To maintain the mechanical pixels at reasonable temperatures, a cooling system such as forced air cooling, liquid immersion, or radiative cooling may be employed.

In some embodiments, surface 26 is highly reflective to avoid excessive heat accumulation in each mechanical pixel. In some of these embodiments, surface 26 is tilted such that the normal to the surface is not aligned with the beam of incoming light 21. In this manner, light reflected from the surface 26 is directed away from the beam of light passing through the programmable aperture; thus minimizing its impact on the performance of the optical system. In some examples, the surface 26 of the mechanical pixel is at least 95% reflective to minimize absorption and accumulation of heat within the mechanical pixel. In the embodiment depicted in FIGS. 1-4, surface 26 of each mechanical pixel is 1.2 millimeters by 1.2 millimeters.

Figure 4:
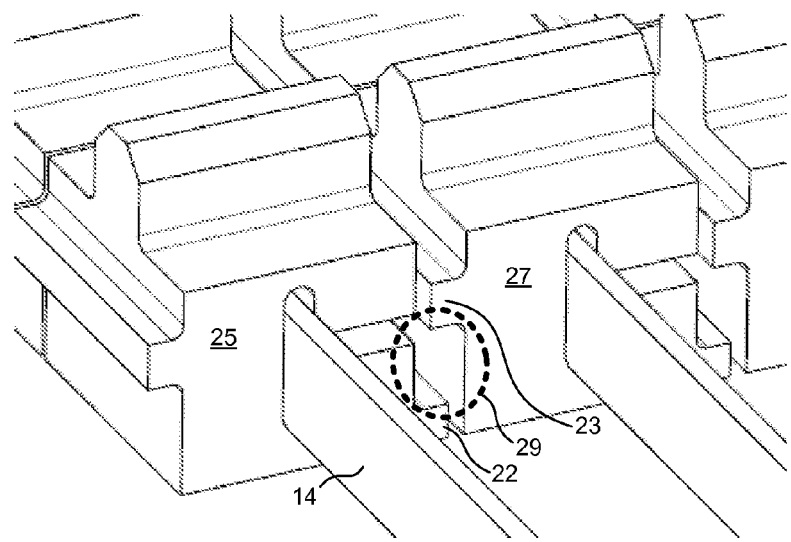
FIG. 4 illustrates a more detailed view of mechanical pixel elements and linear guiding elements associated with the embodiment described with reference to FIG. 1.

In addition, mechanical pixel 25 includes one or more protrusion features 22 and 23 configured to overlap with complementary features located on an adjacent mechanical pixel. For example, as illustrated in FIG. 4, pixel 25 is located adjacent to pixel 27. Protrusion feature 22 of pixel 25 overlaps protrusion feature 23 of pixel 27. In combination, these complementary features create a light trap 29 that prevents the transmission of light through any nominal gap between pixels 25 and 27 along the linear guiding elements. In one embodiment, the overlap between protrusion feature 22 of pixel 25 and protrusion feature 23 of pixel 27 is approximately 0.10 millimeters. Similarly, complementary protrusion features may be included on the pixel faces orthogonal to the linear guiding elements to prevent the transmission of light through any nominal gap between pixels positioned adjacent to one another along the same linear guiding element. In one embodiment, the overlap between these complementary protrusion features is approximately 0.05 millimeters.

FIG. 4 also depicts linear guiding element 14 associated with the embodiment described with reference to FIG. 1 in greater detail. In the embodiment depicted in FIG. 1, each linear guiding element is a wire element stretched across the aperture area. As depicted in FIG. 4, the cross-section of wire element 14 is rectangular in shape to constrain the position of each mechanical pixel in five degrees of freedom while presenting a small cross-sectional area exposed to the incoming beam of light. In one embodiment, the wire element is a stainless steel wire having a cross-section of 0.1 millimeters by 0.4 millimeters.

Figure 5:
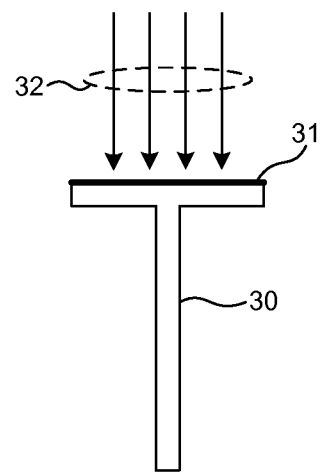
FIG. 5 is a diagram illustrative of a cross-sectional view of a T-shaped linear guiding element in one exemplary embodiment.

Although, a rectangular cross-section is depicted, many other cross-sectional shapes may be contemplated. For example, FIG. 5 depicts a cross-section of a T-shaped wire element 30. The flange of the T-shaped wire element 30 faces the beam of incoming light 32. Although such a T-shaped cross-section may block more light than the rectangular cross-section depicted in FIG. 4, it may be desirable to prevent incoming light from grazing the side of the wire element. Such grazing reflections may be particularly harmful to measurements performed by an optical inspection system operating in a dark field modality. The surface 31 of wire element 30 may be highly absorptive, or treated with a highly absorptive coating, to absorb incoming light. In this manner, light that is blocked by the wire element is absorbed and stray reflections that may interfere with the performance of the optical inspection system are minimized. When surface 31 exposed to the beam of incoming light 32 is highly absorptive, wire element 31 will accumulate significant heat due to the high intensity nature of light 32 employed in typical semiconductor inspection systems. To maintain the mechanical pixels at reasonable temperatures, a cooling system such as forced air cooling, liquid immersion, or radiative cooling may be employed.

Figure 6:
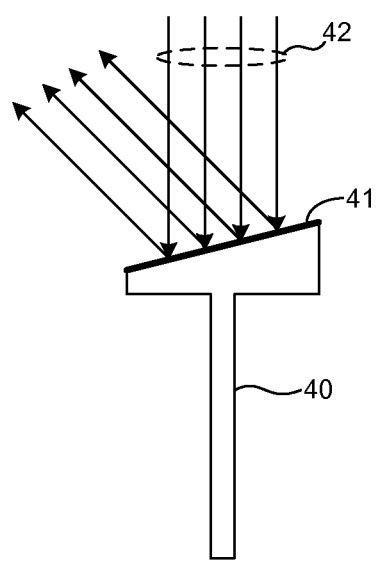
FIG. 6 is a diagram illustrative of a cross-sectional view of a T-shaped linear guiding element in another exemplary embodiment.

FIG. 6 depicts a cross-section of another exemplary wire element 40. The flange of wire element 40 faces the beam of incoming light 42. However, the surface 41 exposed the beam of incoming light 42 is tilted such that the normal to the surface is not aligned with the beam of incoming light 42. In this manner, light reflected from the surface 41 is directed away from the beam of light passing through the programmable aperture; thus minimizing its impact on the performance of the optical system. In some embodiments, surface 41 is highly reflective to avoid excessive heat accumulation in each wire element.

In some other embodiments, the linear guiding elements are extensible structures (e.g., telescoping beams) positioned across the aperture area. The extensible structures can be positioned across the aperture area at different distances. In addition, the locations of the mechanical pixels attached to each extensible structure can be reconfigured. In this manner, the aperture can be reconfigured to realize any number of different aperture shapes.

The programmable aperture system depicted in FIG. 1 maximizes optical transmission efficiency through aperture openings and minimizes optical transmission through portions of the aperture that are blocked by the mechanical pixels. As described hereinbefore, the programmable aperture system includes features to minimize stray light, minimize optical aberrations, and withstand high optical power densities over a range of wavelengths.

In addition, in some embodiments, the programmable aperture system includes shaped optical elements with variably attenuating, polarizing, spectral, phase, and/or gradient properties (e.g., polarizing apertures, apodized apertures, dichroic apertures, or phase plates).

Figure 7:
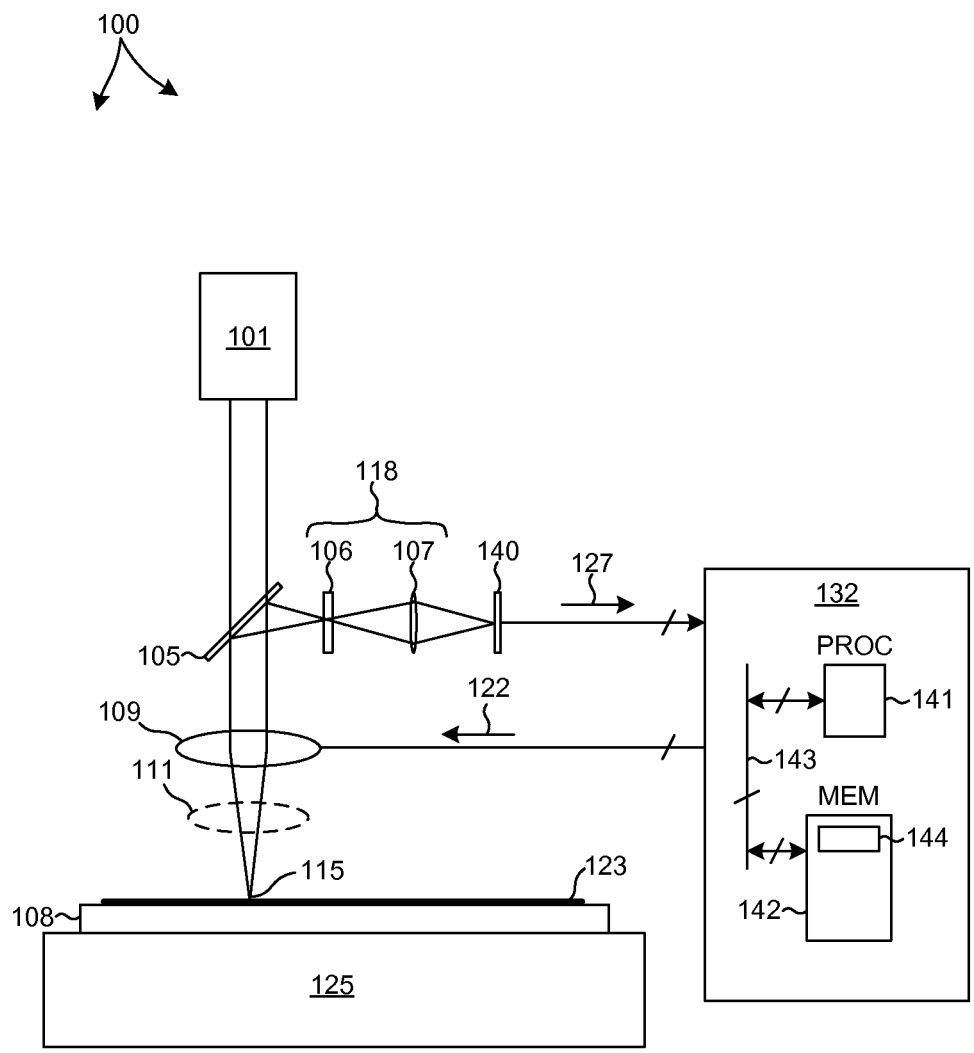
FIG. 7 is a diagram illustrative of an exemplary inspection system 100 including a programmable aperture system as described with reference to FIGS. 1-4.

FIG. 7 illustrates an exemplary inspection system 100 including a programmable aperture system as described with reference to FIGS. 1-4. A programmable aperture system may be located in any accessible pupil plane of inspection system 100. In some embodiments, a programmable aperture system 10 is located in an illumination path of inspection system 100. In some embodiments, a programmable aperture system 10 is located in a collection path of inspection system 100. In some embodiments, a programmable aperture system is located in both the illumination path and collection path of inspection system 100. In some embodiments, any programmable aperture system is located in either or both the illumination path and the collection path, and not in the common path. However, in some embodiments, a programmable aperture system may be located in the common path.

In a further embodiment, full illumination is provided to the wafer 123 and any programmable aperture system is located in the collection path. However, in some embodiments, a programmable aperture system may be located in the illumination path and full collection light is provided to the detector.

Inspection system 100 may be configured to operate in a bright field mode, a dark field mode, or both. Varying sizes and shapes of optical apertures can be applied in both brightfield and darkfield optical modes. The use of special aperture sizes and shapes area enhances signal to noise ratios in optical inspection systems. For simplification, some optical components of system 100 have been omitted. By way of example, folding mirrors, polarizers, beam forming optics, additional light sources, additional collectors, and additional detectors may also be included. All such variations are within the scope of the invention described herein. The inspection system described herein may be used for measuring or inspecting patterned, as well as unpatterned wafers.

As illustrated in FIG. 7, a wafer 123 is illuminated by a normal incidence beam 111 generated by one or more illumination sources 101. Alternatively, the illumination subsystem may be configured to direct the beam of light to the specimen at an oblique angle of incidence. In some embodiments, system 100 may be configured to direct multiple beams of light to the specimen such as an oblique incidence beam of light and a normal incidence beam of light. The multiple beams of light may be directed to the specimen substantially simultaneously or sequentially.

Illumination source 101 may include, by way of example, a laser sustained plasma light source, a laser, a diode laser, a helium neon laser, an argon laser, a solid state laser, a diode pumped solid state (DPSS) laser, a xenon arc lamp, a gas discharging lamp, and LED array, or an incandescent lamp. The light source may be configured to emit near monochromatic light or broadband light. In general, the illumination subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm). Therefore, if the light source is a broadband light source, the illumination subsystem may also include one or more spectral filters that may limit the wavelength of the light directed to the specimen. The one or more spectral filters may be bandpass filters and/or edge filters and/or notch filters.

A beam splitter 105 directs the illumination light to an objective lens 109. Objective lens 109 focuses the illumination light 111 onto a wafer 123 at illumination spot 115. In one embodiment, objective 109 includes a programmable aperture system 10. In this manner, illumination spot 115 is shaped and sized by the projection of light transmitted through the programmable aperture system 10 onto the surface of wafer 123.

In some embodiments, reflected/scattered light is collected and detected from all of the area of illumination spot 115 over a particular sample period by inspection system 100. In this manner, as much light as possible is collected by inspection system 100. However, in some other embodiments, reflected/scattered light is collected and detected from a portion of the area of illumination spot 115 over a particular sample period by inspection system 100. System 100 includes collection optics 118 to collect light scattered and/or reflected by wafer 123 during the scan and to focus the collected light onto detector 140. An output signal 127 generated by detector 140 is supplied to a computer 132 for signal processing to determine the presence of anomalies and their characteristics.

Collection optics 118 may include a lens, a compound lens, or any appropriate lens known in the art. Alternatively, any element of collection optics 118 may be a reflective or partially reflective optical component, such as a mirror. In addition, although particular collection angles are illustrated in FIG. 7, it is to be understood that the collection optics may be arranged at any appropriate collection angle. The collection angle may vary depending upon, for example, the angle of incidence and/or topographical characteristics of the specimen.

Detector 140 generally functions to convert the scattered light into an electrical signal, and therefore, may include substantially any photodetector known in the art. However, a particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may increase the signal-to-noise ratio and throughput of the system. However, other detectors such as spectrometers, charge-coupled device (CCD) cameras, photodiodes, phototubes and photomultiplier tubes (PMTs) may be used, depending on the amount of light available for inspection and the type of inspection being performed. In at least one embodiment of the invention, a photomultiplier tube is used for detecting light scattered from a specimen.

In the depicted embodiment, a detector is associated with a particular illumination spot (e.g., detector 140 is a detector employed to generate an output signal associated with an inspection area illuminated by illumination spot 115). However, in other embodiments, additional detectors may be employed to each generate an output signal associated with an illumination spot. For example, multiple detectors may be employed to detect light collected from an inspection area illuminated by illumination spot 115, each at different collection angles. Detector 140 may generate a single output signal to enable high throughput or may be an imaging detector (i.e., a detector that generates a number of separate output signals indicative of light collected over different inspection areas illuminated by illumination spot 115).

System 100 also includes various electronic components (not shown) needed for processing the scattered signals detected by detector 140. For example, system 100 may include amplifier circuitry to receive output signal 127 from detector 140 and to amplify the output signal by a predetermined amount. In addition, an analog-to-digital converter (ADC) (not shown) is included to convert the amplified signals into a digital format suitable for use within processor 141. In one embodiment, the processor may be coupled directly to an ADC by a transmission medium. Alternatively, the processor may receive signals from other electronic components coupled to the ADC. In this manner, the processor may be indirectly coupled to the ADC by a transmission medium and any intervening electronic components.

In general, processor 141 is configured to detect features, defects, or light scattering properties of the wafer using electrical signals obtained from each detector. The signals produced by the detector are representative of the light detected by a single detector (e.g., detector 140). The processor may include any appropriate processor known in the art. In addition, the processor may be configured to use any appropriate defect detection algorithm or method known in the art. For example, the processor may use a die-to-database comparison or a thresholding algorithm to detect defects on the specimen.

In addition, inspection system 100 may include peripheral devices useful to accept inputs from an operator (e.g., keyboard, mouse, touchscreen, etc.) and display outputs to the operator (e.g., display monitor). Input commands from an operator may be used by processor 141 to adjust threshold values used to control illumination power. The resulting power levels may be graphically presented to an operator on a display monitor.

System 100 can use various imaging modes, such as bright field, dark field, and confocal. For example, in the embodiment depicted in FIG. 7, detector 140 generates a bright field signal. As illustrated in FIG. 7, some amount of light scattered from the surface of wafer 123 at a narrow angle is collected by objective lens 109. This light passes back through objective lens 109 and impinges on beam splitter 105. Beam splitter 105 transmits a portion of the light to collection optics 118, which in turn focuses the light onto detector 140. In this manner a bright field signal is generated by detector 140. Collection optics 118 includes imaging lens 107 that images the reflected light collected by objective lens 109 onto detector array 140. In some embodiments, an aperture 106 is placed at the back focal plane of objective lens 109. In some embodiments, aperture 106 is a programmable aperture system 10 located at the back focal plane of objective lens 109. Various imaging modes such as bright field, dark field, and phase contrast can be implemented by using different apertures. In another example (not shown), a detector generates dark field images by imaging scattered light collected at larger field angles. In another example, a pinhole that matches the incident spot 115 can be placed in front of a detector (e.g., detector 140) to generate a confocal image.

In the embodiment illustrated in FIG. 7, wafer positioning system 125 moves wafer 123 supported by wafer chuck 108 under a stationary beam of illumination light 111.

In a further embodiment, inspection system 100 includes one or more computing systems 132 employed to perform measurements and to generate command signals 122 communicated to the actuator subsystem of a programmable aperture system 10 located within objective 109 to control a rearrangement of position of the one or more mechanical pixel elements. In this manner, computing system 132 controls the configuration of programmable aperture system 10. In particular, one or more computing systems 132 may be employed to perform aperture reconfiguration functionality, and control various parameters of the measurement system. The one or more computing systems 132 may be communicatively coupled to detector 140 and programmable aperture system 10 located within objective 109. In one aspect, the one or more computing systems 132 are configured to receive measurement data 127 associated with a measurement of the wafer 123. In one example, the measurement data 127 includes an indication of the measured spectral response of the specimen based on the one or more sampling processes from spectrometer 140. The one or more computer systems 132 are further configured to determine a value of at least one CD parameter value associated with the wafer 123.

It should be recognized that the various steps described throughout the present disclosure may be carried out by a single computer system or, alternatively, a multiple computer system. Moreover, different subsystems of the system 100, such as the programmable aperture system 10, may include a computer system suitable for carrying out at least a portion of the steps described herein. Therefore, the aforementioned description should not be interpreted as a limitation on the present invention but merely an illustration.

In addition, the computer system 132 may be communicatively coupled to the detector 140, illumination source 101, any programmable aperture system, or any other element of inspection system 100 in any manner known in the art. For example, the one or more computing systems 132 may be coupled to a computing system of a spectrometer 140, a computing system of the illumination source 101, or a computing system of the programmable aperture system 10. In another example, the detector 140, illuminator 101, and programmable aperture system 10 may be controlled by a single computer system. In this manner, the computer system 132 of the system 100 may be coupled to a single computer system.

The computer system 132 of the system 100 may be configured to receive and/or acquire data or information from the subsystems of the system (e.g., detector 140, illuminator 101, a programmable aperture system 10, and the like) by a transmission medium that may include wireline and/or wireless portions. In this manner, the transmission medium may serve as a data link between the computer system 132 and other subsystems of the system 100. Further, the computing system 132 may be configured to receive aperture configuration data via a storage medium (i.e., memory). For instance, aperture configuration data may be stored in a permanent or semi-permanent memory device (e.g., memory 142).

Moreover, the computer system 132 of the system 100 may be configured to receive and/or acquire data or information from other systems (e.g., aperture configuration data) by a transmission medium that may include wireline and/or wireless portions. In this manner, the transmission medium may serve as a data link between the computer system 132 and external systems.

The computing system 132 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 144 implementing methods and functionality such as those described herein may be stored in memory 142 and transmitted over a carrier medium (e.g., bus 143) to processor 141 for execution. The carrier medium may be a transmission medium such as a wire, cable, or wireless transmission link. The carrier medium may also include a computer-readable medium such as a read-only memory, a random access memory, a magnetic or optical disk, or a magnetic tape.

In some examples, computing system 132 is programmed to generate control signals to control the movements of actuators of programmable aperture system 10 to achieve a particular configuration of mechanical pixels across the aperture. Computing system 132 may also receive data indicative of the position of these elements.

Figure 8:
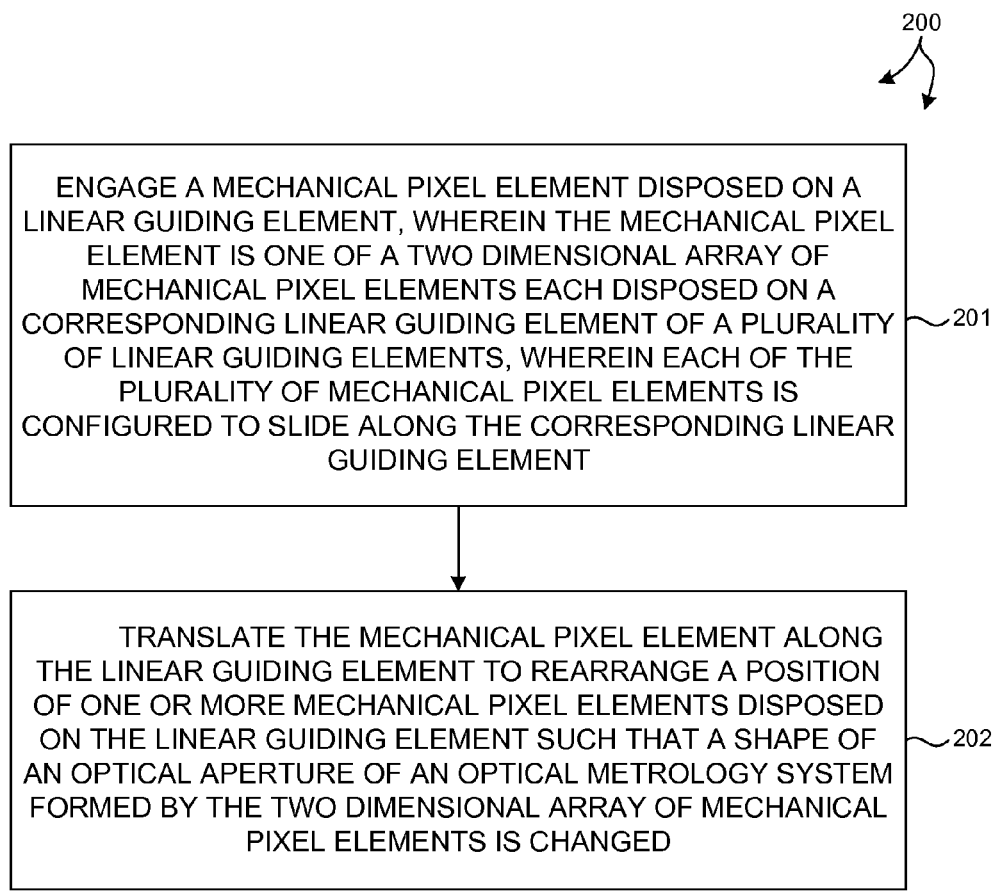
FIG. 8 is a flowchart illustrative of an exemplary method 200 of reconfiguring an aperture of an optical inspection system.

FIG. 8 illustrates a method 200 suitable for implementation by the programmable aperture system of the present invention. In one aspect, it is recognized that data processing blocks of method 200 may be carried out via a pre-programmed algorithm executed by one or more processors of computing system 132. While the following description is presented in the context of system 10, it is recognized herein that the particular structural aspects of system 10 do not represent limitations and should be interpreted as illustrative only.

In block 201, a mechanical pixel element disposed on a linear guiding element is engaged. The mechanical pixel element is one of a two dimensional array of mechanical pixel elements. Each of the mechanical pixel elements is disposed on a corresponding linear guiding element of a plurality of linear guiding elements. Each of the plurality of mechanical pixel elements is configured to slide along the corresponding linear guiding element.

In block 202, the mechanical pixel element is translated along the linear guiding element to rearrange the position of one or more mechanical pixel elements disposed on the linear guiding element. As a result, a shape of an optical aperture of an optical inspection system formed by the two dimensional array of mechanical pixel elements is changed.

A system implementing the methods described herein may be configured in a number of different ways. For example, the system may include any suitable combination of actuators to locate mechanical pixels over an aperture of an optical inspection system, and thus to condition light directed to or collected from the specimen under measurement.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

In general, a wafer includes multiple layers. The measurement of the relative positions of these layers is commonly termed an "overlay measurement application." Each layer includes periodic structures, and the relative positions of the layers are measured as a shift in one direction or more directions. Thus, in general, and for purposes of this patent document, overlay measurements are regarded as a CD measurement, where the position shifts of the periodic structures are the CD parameters to be measured.

As described herein, the term "critical dimension application" or "critical dimension measurement application" includes any critical dimension measurement.

As described herein, the term "inspection system" includes any system employed at least in part to characterize a specimen in any aspect. However, such terms of art do not limit the scope of the term "inspection system" as described herein. The term "specimen" is used herein to refer to a site on a wafer, a reticle, or any other sample that may be processed (e.g., printed or inspected for defects) by means known in the art.

In addition, the inspection system 100 may be configured for measurement of patterned wafers and/or unpatterned wafers. The inspection system may be configured as a LED inspection tool, edge inspection tool, backside inspection tool, macro-inspection tool, or multi-mode inspection tool (involving data from one or more platforms simultaneously), and any other metrology or inspection tool that benefits from a programmable aperture system.

Various embodiments are described herein for a semiconductor processing system (e.g., an inspection system, a metrology system, or a lithography system) that may be used for processing a specimen. In one example, a programmable aperture system as described herein may be employed to condition illumination light transmitted from an illumination source to a reticle in a lithographic system for improved patterning on a wafer being processed by the lithographic system.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A programmable optical aperture mechanism comprising:
   a plurality of linear guiding elements disposed in a first direction;
   a plurality of mechanical pixel elements disposed on each of the plurality of linear guiding elements, wherein each of the plurality of mechanical pixel elements is configured to slide along a corresponding linear guiding element, and wherein any number of the plurality of pixel elements is positioned to be exposed to a beam of light passing through an aperture area of the programmable optical aperture mechanism;
   an actuator subsystem configured to selectively translate one or more mechanical pixel elements along one or more corresponding linear guiding elements; and
   a controller configured to generate command signals communicated to the actuator subsystem to control a rearrangement of position of the one or more mechanical pixel elements.

2. The programmable optical aperture mechanism of claim 1, wherein the guiding elements are wire elements positioned across the aperture area.

3. The programmable optical aperture mechanism of claim 1, wherein the guiding elements are extensible structures configured to be programmably positioned across the aperture area.

4. The programmable optical aperture mechanism of claim 1, wherein each of the mechanical pixel elements includes one or more protrusion features configured to overlap a portion of a first adjacent mechanical pixel element.

5. The programmable optical aperture mechanism of claim 4, wherein the one or more protrusion features are configured to overlap a portion of the first adjacent mechanical pixel element in a first direction and a portion of a second adjacent mechanical pixel element in a second direction.

6. The programmable optical aperture mechanism of claim 5, wherein the first direction is perpendicular to the second direction and the first and second directions are perpendicular to a direction of a beam of light passing through the programmable optical aperture mechanism.

7. The programmable optical aperture mechanism of claim 1, wherein the surface of each of the mechanical pixel elements exposed to a beam of light passing through the programmable optical aperture mechanism is at least 95% reflective.

8. The programmable optical aperture mechanism of claim 1, wherein the actuator subsystem includes a linear actuator configured to move a frame in a first direction and an array of solenoid actuators mounted to the frame, wherein each of the array of solenoid actuators is configured to move in a second direction and engage at least one mechanical pixel element.

9. The programmable optical aperture mechanism of claim 2, wherein each of the wire elements includes an optically absorptive surface exposed to a beam of light passing through the programmable optical aperture mechanism.

10. The programmable optical aperture mechanism of claim 2, wherein each of the wire elements includes a highly reflective surface exposed to a beam of light passing through the programmable optical aperture, wherein the highly reflective surface is oriented such that an amount of light reflected from the surface is directed away from the beam of light.

11. The programmable optical aperture mechanism of claim 2, wherein each of the wire elements includes a flange structure configured to prevent light from a beam of light passing through the programmable optical aperture from grazing any other surface of the wire element.

12. A method comprising:
   engaging a mechanical pixel element disposed on a linear guiding element, wherein the mechanical pixel element is one of a two dimensional array of mechanical pixel elements each disposed on a corresponding linear guiding element of a plurality of linear guiding elements, wherein each of the plurality of mechanical pixel elements is configured to slide along the corresponding linear guiding element; and translating the mechanical pixel element along the linear guiding element to rearrange a position of one or more mechanical pixel elements disposed on the linear guiding element such that a shape of an optical aperture of an optical inspection system formed by the two dimensional array of mechanical pixel elements is changed.

13. The method of claim 12, further comprising:

generating command signals communicated to an actuator subsystem to control the engaging and the translating of the mechanical pixel element.

14. The method of claim 12, wherein the plurality of linear guiding elements is an array of wire elements aligned in parallel and positioned across the optical aperture.

15. The method of claim 14, wherein each of the wire elements includes a flange structure configured to prevent incoming light from grazing a surface of the wire element.

16. The method of claim 12, wherein each of the mechanical pixel elements includes one or more protrusion features configured to overlap a portion of an adjacent mechanical pixel element.

17. The programmable optical aperture mechanism of claim 1, wherein the aperture area of the programmable optical aperture mechanism is positioned in any of an optical illumination path and an optical collection path of an optical inspection system, the optical inspection system including an illumination source configured to generate an amount of illumination light projected to a surface of a specimen, and a detector configured to detect an amount of light collected from the surface of the specimen.

18. The programmable optical aperture mechanism of claim 17, wherein the optical inspection system is operable in any of a dark field and a bright field imaging mode.

* * * * *